(12) United States Patent
Hsiao

(10) Patent No.: US 10,004,443 B2
(45) Date of Patent: Jun. 26, 2018

(54) PROTECTING MECHANISM FOR BLOOD SAMPLING DEVICE

(71) Applicant: MEDIFUN CORPORATION, Taichung (TW)

(72) Inventor: Shao-Lun Hsiao, Taichung (TW)

(73) Assignee: MEDIFUN CORPORATION, Taichung (TW)

( * ) Notice: Subject to any disclaimer, the term of this patent is extended or adjusted under 35 U.S.C. 154(b) by 575 days.

(21) Appl. No.: 14/623,436

(22) Filed: Feb. 16, 2015

(65) Prior Publication Data

US 2015/0272491 A1    Oct. 1, 2015

(30) Foreign Application Priority Data

Mar. 27, 2014   (TW) .............................. 103205312 U

(51) Int. Cl.
*A61B 5/15*      (2006.01)
*A61B 5/151*     (2006.01)

(52) U.S. Cl.
CPC ...... *A61B 5/150022* (2013.01); *A61B 5/1519* (2013.01); *A61B 5/15111* (2013.01); *A61B 5/15117* (2013.01); *A61B 5/15194* (2013.01); *A61B 5/150412* (2013.01); *A61B 5/150648* (2013.01)

(58) Field of Classification Search
None
See application file for complete search history.

(56) References Cited

U.S. PATENT DOCUMENTS

2007/0083222 A1* 4/2007 Schraga ........... A61B 5/150022
606/181

* cited by examiner

*Primary Examiner* — Matthew Kremer

(57) ABSTRACT

A protecting mechanism for a blood sampling device contains: a trigger unit and a switching assembly. The trigger unit includes a lancet holder, a triggering shaft, and a resilient element. The lancet holder has a launching portion, a first outer protrusion, a through orifice, and a first inner shoulder, wherein a bottom end of the triggering shaft moves in the through hole, and the triggering shaft has a first outer shoulder for engaging with the first inner shoulder of lancet holder, the resilient element is fitted with the triggering shaft and abuts against the lancet holder by ways of its bottom end. The switching assembly includes a fixing jacket having an abutting portion, a rotating tube having a first inner protrusion and two opposite second inner protrusions, and a driving sheath having two stopping sets, wherein each stopping set has two second outer protrusions.

15 Claims, 10 Drawing Sheets

US 10,004,443 B2

PROTECTING MECHANISM FOR BLOOD SAMPLING DEVICE

FIELD OF THE INVENTION

The present invention relates to a blood sampling device, and more particularly to a protecting mechanism for the blood sampling device.

BACKGROUND OF THE INVENTION

A conventional blood sampling device is employed to sample patient's blood after inserting into skin, and its lancet is discarded after use.

However, the conventional blood sampling device is not provided with a protecting mechanism for preventing the lancet from injuring medical personnel, thus increasing using danger.

The present invention has arisen to mitigate and/or obviate the afore-described disadvantages.

SUMMARY OF THE INVENTION

The primary objective of the present invention is to provide a protecting mechanism for a blood sampling device which prevents a removal of a lancet by using a switching assembly while triggering the lancet and avoids triggering the lancet while retracting the lancet.

To obtain the above objective, a protecting mechanism for a blood sampling device provided by the present invention contains: a trigger unit and a switching assembly.

The trigger unit includes a lancet holder, a triggering shaft, and a resilient element. The lancet holder has a launching portion and a first outer protrusion opposite to the launching portion, the lancet holder also has a through orifice defined therein and a first inner shoulder defined on a top end of the through orifice, wherein a bottom end of the triggering shaft moves in the through hole, and the triggering shaft has a first outer shoulder arranged on an outer wall thereof to engage with the first inner shoulder of lancet holder, the resilient element is fitted with the triggering shaft and abuts against the lancet holder by ways of its bottom end.

The switching assembly includes a fixing jacket, a rotating tube, and a driving sheath. The fixing jacket is fitted with the lancet holder and has an abutting portion, the rotating tube is rotatably fitted with the fixing jacket between a starting position and a retracting position, and the rotating tube has a first inner protrusion arranged on an inner wall thereof and has two opposite second inner protrusions formed on the inner wall thereof. The driving sheath is fitted on a top end of the triggering shaft and contacts with a top end of the resilient element, and the driving sheath has two stopping sets arranged on an outer wall thereof, wherein each stopping set has two second outer protrusions.

Preferably, the lancet holder further a cutout defined on the first outer protrusion, such that when the rotating tube is located at the starting position, the first inner protrusion of the rotating tube moves away from the cutout of the lancet holder to remove from the first outer protrusion of the lancet holder, and when the rotating tube is located at the retracting position, the first inner protrusion of the rotating tube extends into the cutout of the lancet holder to engage with the first outer protrusion of the lancet holder.

Preferably, the rotating tube further has a flexible pressing portion formed on the outer wall thereof, such that when the rotating tube is located at the starting position, the flexible pressing portion presses the launching portion of the lancet holder.

Preferably, the trigger unit further includes a connector fitted with the top end of the triggering shaft and abutting against the driving sheath.

Preferably, the top end of the triggering shaft extends out of the through orifice of the lancet holder and has a second outer shoulder above the first outer shoulder, the connector has a pushing member, and the pushing member has two opposite second inner shoulders arranged on an inner wall thereof to engage with the second outer shoulder of the triggering shaft, and the pushing member also has two opposite extensions extending outwardly from an outer wall thereof, wherein each extension contacts with the two second outer protrusions of each stopping set of the driving sheath.

Preferably, the connector has a housing, and the housing has an aperture and two opposite retainers formed on a peripheral wall of the aperture, wherein each extension has a locking portion for engaging with each retainer of the housing.

Preferably, the trigger unit further includes a cap and a returning spring, and the cap is fitted with the top end of the triggering shaft, the returning spring is fitted on the triggering shaft and is biased against the pushing member and the cap.

DETAILED DESCRIPTION OF THE PREFERRED EMBODIMENTS

Figure 1:
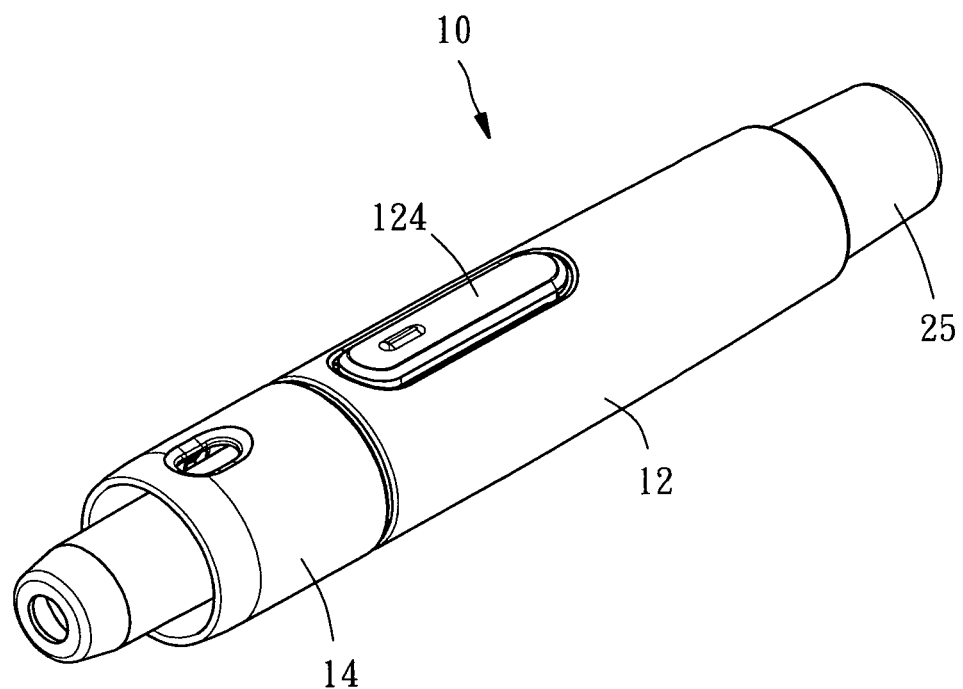
FIG. 1 is a perspective view showing the assembly of a blood sampling device according to a preferred embodiment of the present invention.
Figure 2:
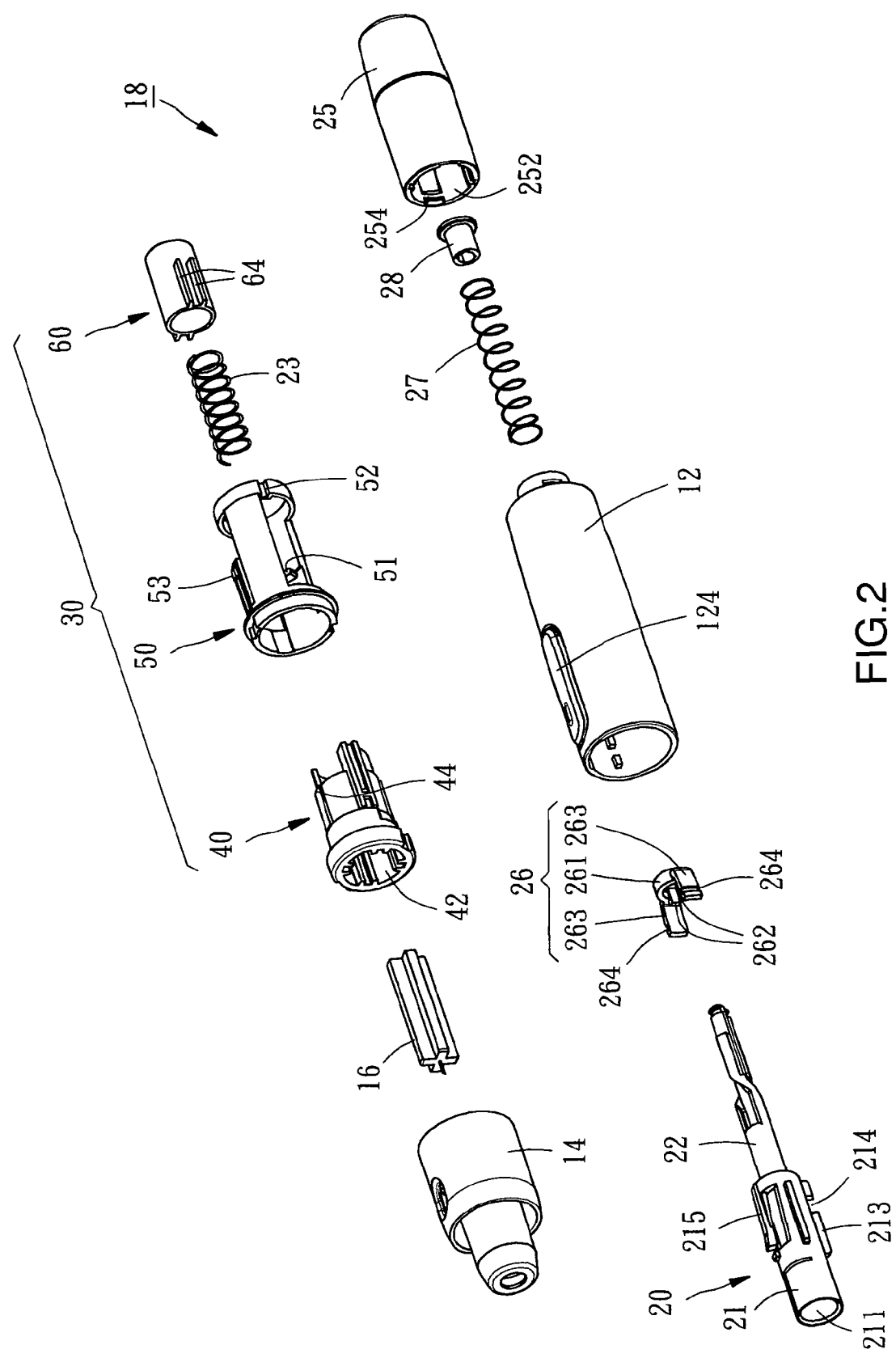
FIG. 2 is a perspective view showing the exploded components of the blood sampling device according to the preferred embodiment of the present invention.

With reference to FIG. 1, a blood sampling device 10 according to a preferred embodiment of the present invention comprises a body 12 and a fitting tube 14 connected with a bottom end of the body 12. Referring further to FIG. 2, a protecting mechanism 18 is mounted in the blood sampling device 10 and includes a trigger unit 20 and a switching assembly 30.

The trigger unit 20 includes a lancet holder 21, a triggering shaft 22, a resilient element 23, and a connector 24.

Figure 3:
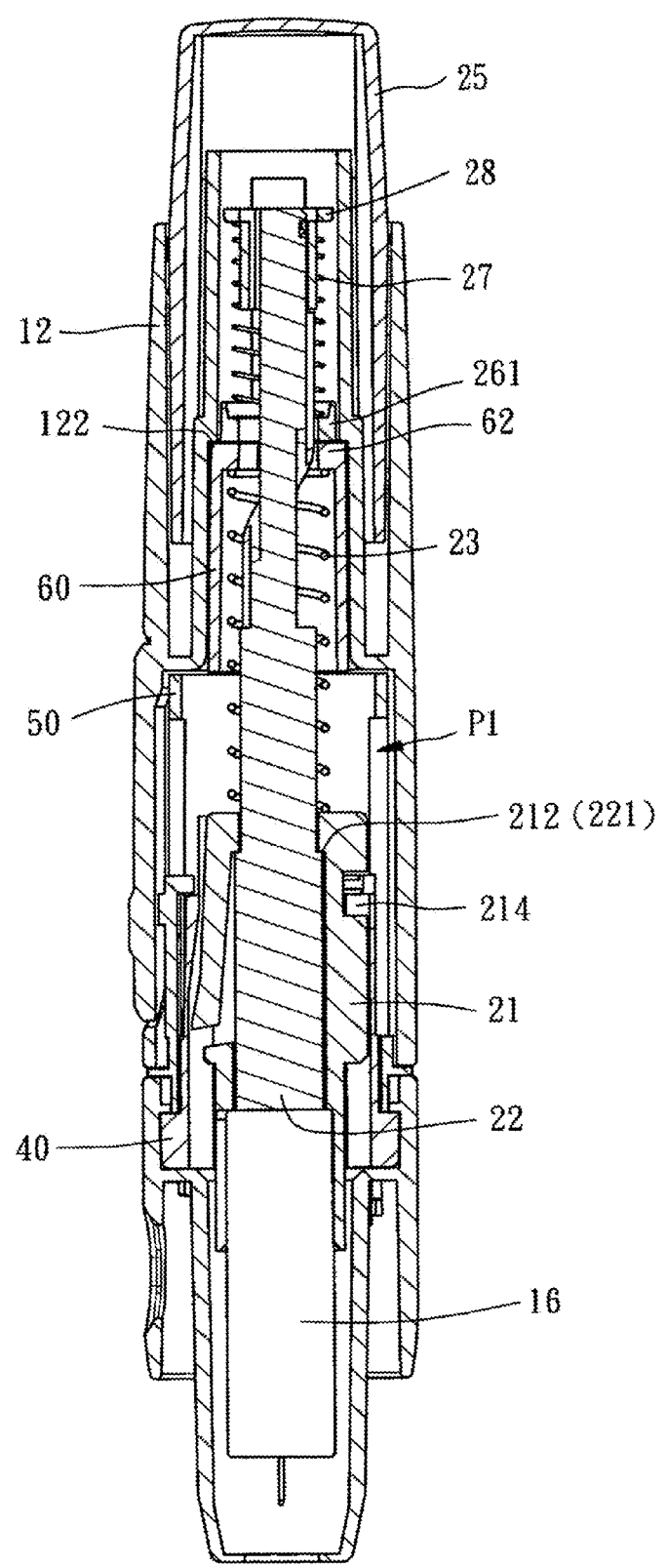
FIG. 3 is a cross sectional view showing the assembly of the blood sampling device according to the preferred embodiment of the present invention.

The lancet holder 21 has a through orifice 211 defined therein to insert a lancet 16, a first inner shoulder 212 defined on a top end of the through orifice 211 (as shown in FIG. 3), a first outer protrusion 213 formed on an outer wall thereof, a cutout 214 defined on the first outer protrusion 213, and a launching portion 215 opposite to the first outer protrusion 213.

As illustrated in FIGS. 2 and 3, the triggering shaft 22 is inserted into the through orifice 211 of the lancet holder 21 to trigger the lancet 16, and a top end of the triggering shaft 22 extends out of the through orifice 211 of the lancet holder 21 and fits with a cap 28. The triggering shaft 22 has a first outer shoulder 221 arranged on an outer wall thereof and has a second outer shoulder 223 above the first outer shoulder 221, wherein the first outer shoulder 221 engages with the first inner shoulder 212 of the lancet holder 21 (as shown in FIG. 3), such that after the triggering shaft 22 is pulled, it drives the lancet holder 21 to move away from the lancet 16.

The resilient element 23 is fitted with the triggering shaft 22 and abuts against a top end of the lancet holder 21 by ways of its bottom end, such that the lancet holder 21 is pushed by the resilient element 23 to drive the triggering shaft 22 to move toward the lancet 16.

Figure 4:
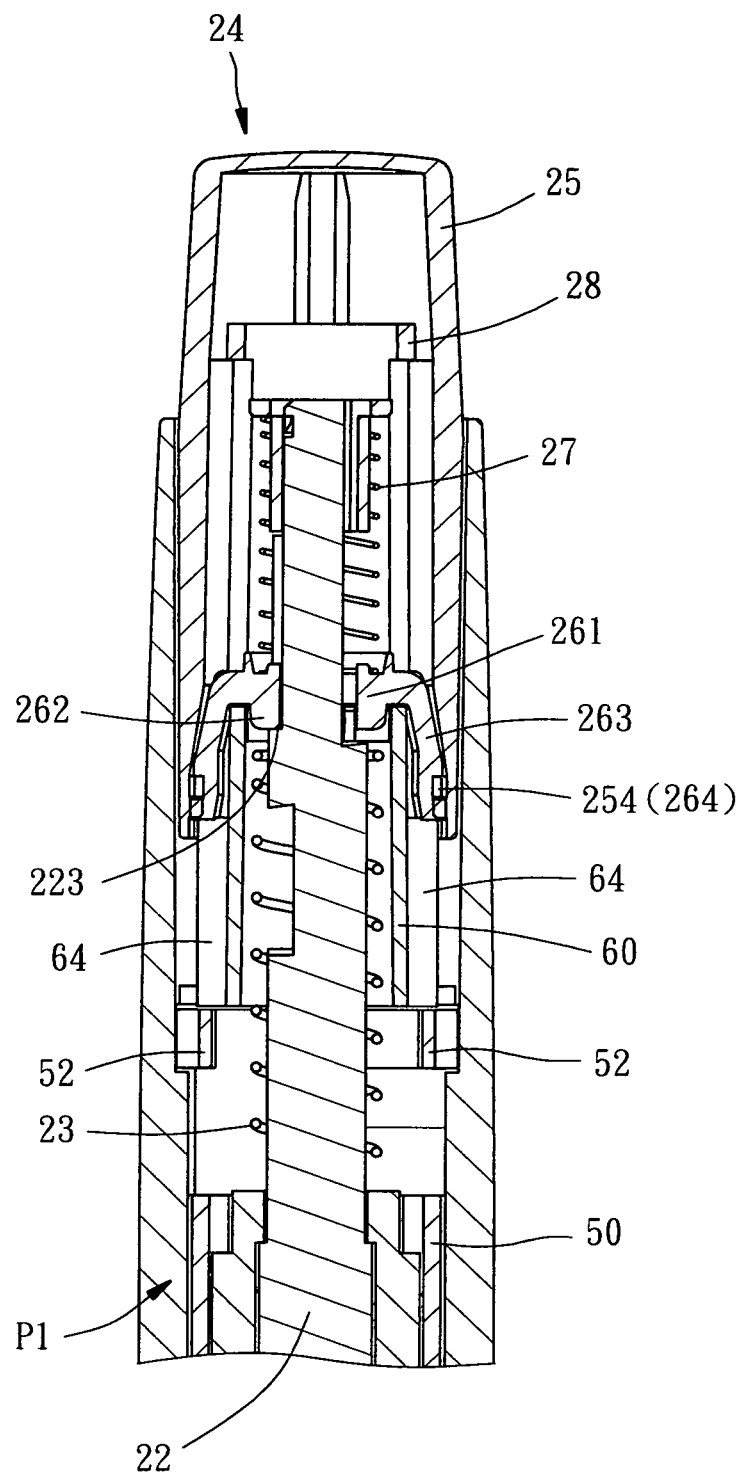
FIG. 4 is another cross sectional view showing the assembly of the blood sampling device according to the preferred embodiment of the present invention.

The connector 24 has a housing 25, a pushing member 26, and a returning spring 27. With reference to FIGS. 2 and 4, the housing 25 has an aperture 252 for fitting with a top end of the body 12 and has two opposite retainers 254 formed on a peripheral wall of the aperture 252. The pushing member 26 has a loop 261 fitted on the top end of the triggering shaft 22 and has two opposite second inner shoulders 262 arranged on an inner wall thereof to engage with the second outer shoulder 223 of the triggering shaft 22. The pushing member 26 also has two opposite extensions 263 extending outwardly from an outer wall of the loop 261, wherein each extension 263 has a locking portion 264 for engaging with each retainer 254 of the housing 25, such that the pushing member 26 is mounted in the aperture 252 of the housing 25. The returning spring 27 is fitted on the triggering shaft 22 and is biased against the loop 261 of the pushing member 26 and the cap 28 to push the triggering shaft 22 to move back to an original position.

The switching assembly 30 includes a fixing jacket 40, a rotating tube 50, and a driving sheath 60.

The fixing jacket 40 is disposed on the bottom end of the body 12 and is fitted into the fitting tube 14. The fixing jacket 40 has an opening 42 defined therein to fit with the lancet holder 21 and has an abutting portion 44 formed on an outer wall thereof to engage with the launching portion 215 of the lancet holder 21, as shown in FIGS. 2 to 6.

The rotating tube 50 is rotatably fitted with the fixing jacket 40 and is defined between the body 12 and the fixing jacket 40. The rotating tube 50 has a first inner protrusion 51 arranged on a middle section of an inner wall thereof and has two opposite second inner protrusions 52 formed on a top end of the inner wall thereof, such that when the rotating tube 50 is located at a starting position P1, as illustrated in FIGS. 2 and 3, the first inner protrusion 51 of the rotating tube 50 moves away from the cutout 214 of the lancet holder 21 to remove from the first outer protrusion 213 of the lancet holder 21, hence the lancet holder 21 moves upwardly and downwardly in the opening 42 of the fixing jacket 40. With reference to FIGS. 2 to 8, when the rotating tube 50 is located at a retracting position P2, the first inner protrusion 51 extends into the cutout 214 of the lancet holder 21 to engage with the first outer protrusion 213 of the lancet holder 21, hence the lancet holder 21 does not move upwardly and downwardly in the opening 42 of the fixing jacket 40.

The rotating tube 50 further has a flexible pressing portion 53 formed on the outer wall thereof and corresponding to the abutting portion 44 of the fixing jacket 40.

Figure 9:
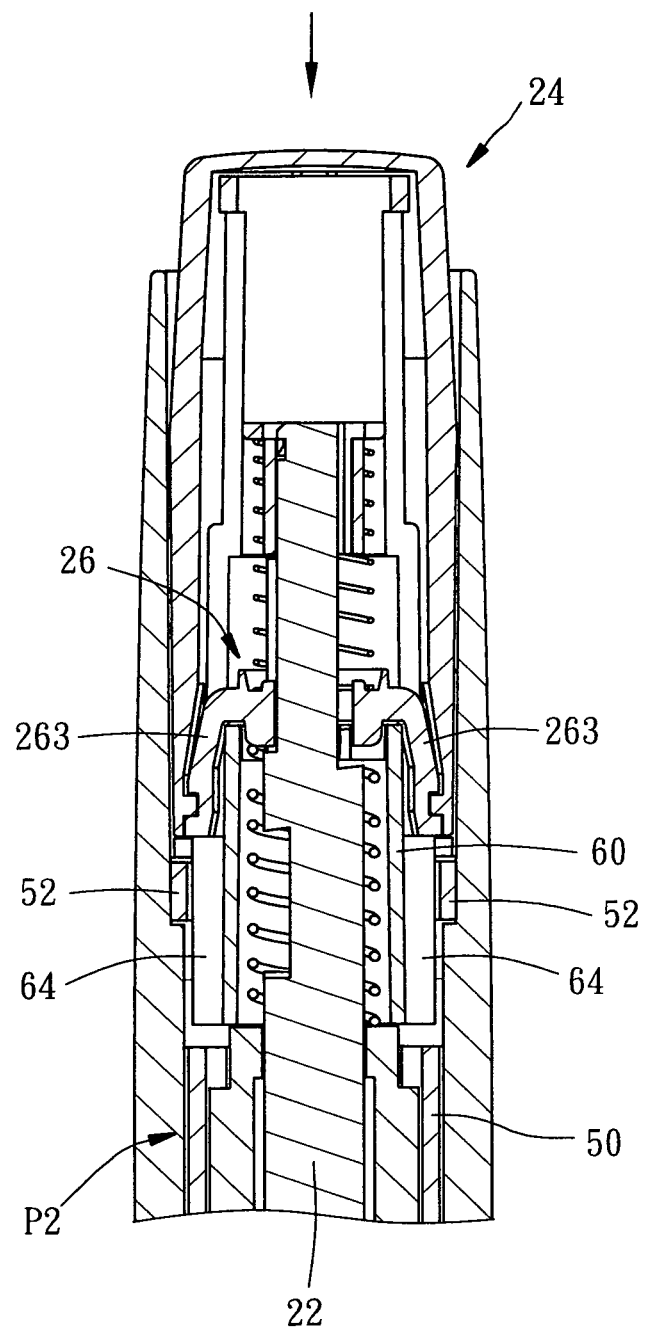
FIG. 9 is another cross sectional view showing the operation of the blood sampling device according to the preferred embodiment of the present invention.

The driving sheath 60 is fitted on the triggering shaft 22 and abuts against an internal rib 122 of the body 12 (as shown in FIG. 3), the driving sheath 60 has an end face 62 for contacting with a top end of the resilient element 23 and the loop 261 of the pushing member 26 (as illustrated in FIG. 3). The driving sheath 60 also has two stopping sets (i.e., each stopping set has two second outer protrusions 64, as illustrated in FIG. 2) arranged on an outer wall thereof, wherein the two second outer protrusion 64 of each stopping set are defined between each second inner protrusion 52 of the rotating tube 50 and each extension 263 of the pushing member 26, such that when the rotating tube 50 is located at the starting position P1, as shown in FIG. 4, the two second outer protrusions 64 of each stopping set of the driving sheath 60 are stopped by each second inner protrusion 52 of the rotating tube 50, and then the driving sheath 60 does not move downwardly. Referring to FIG. 9, when the rotating tube 50 is located at the retracting position P2, the two second outer protrusions 64 of each stopping set of the driving sheath 60 are not stopped by each second inner protrusion 52 of the rotating tube 50, and then the driving sheath 60 is pushed by each extension 263 of the pushing member 26 to move downwardly.

Figure 5:
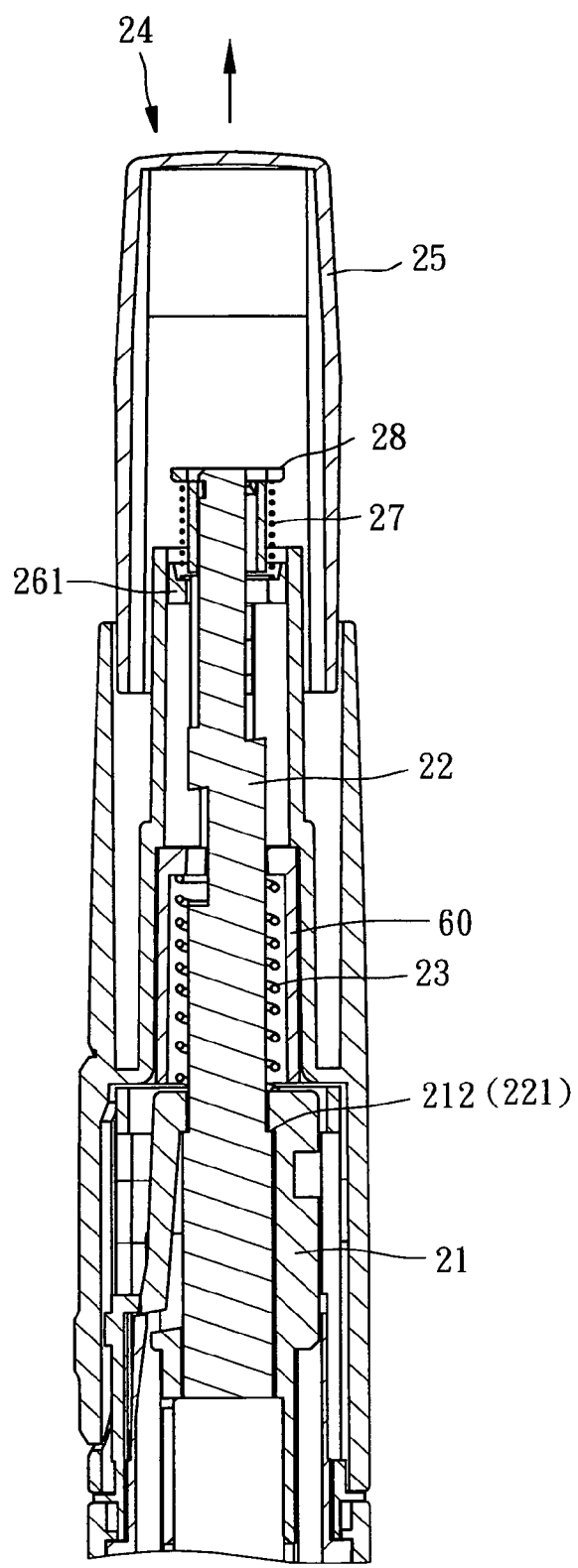
FIG. 5 is a cross sectional view showing the operation of the blood sampling device according to the preferred embodiment of the present invention.
Figure 6:
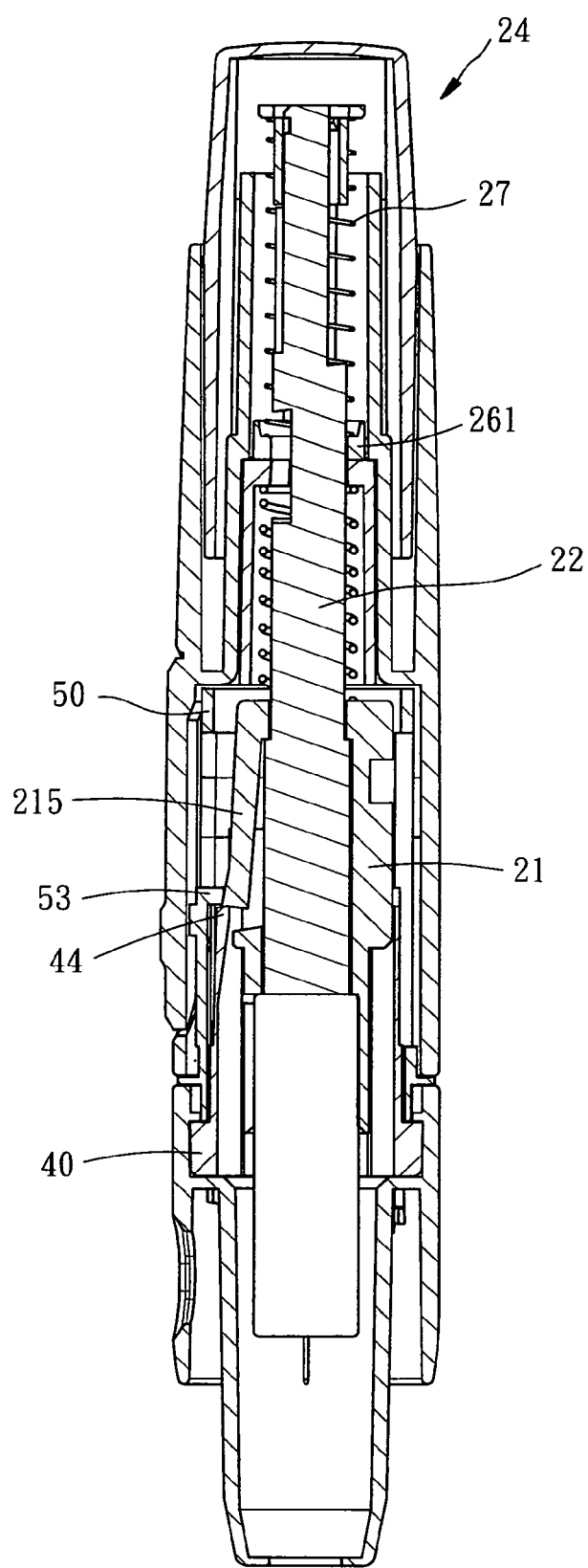
FIG. 6 is another cross sectional view showing the operation of the blood sampling device according to the preferred embodiment of the present invention.

In operation, as shown in FIG. 3, the rotating tube 50 is rotated toward the starting position P1 so that the lancet holder 21 moves upwardly and downwardly in the opening 42 of the fixing jacket 40, and then the housing 25 of the connector 24 is pulled, as illustrated in FIG. 5, such that the connector 24 pushes the returning spring 27 to move upwardly by using the loop 261 of the pushing member 26, and then the returning spring 27 pushes the cap 28 to move upwardly so that the triggering shaft 22 is driven by the cap 28 to move upwardly. In the meantime, the triggering shaft 22 pushes the lancet holder 21 by engaging the first outer shoulder 221 with the first inner shoulder 212 of the lancet holder 21. Since the driving sheath 60 is fixed, the resilient element 23 is pressed by the lancet holder 21, and when the launching portion 215 of the lancet holder 21 engages with the abutting portion 44 of the fixing jacket 40, it is pressed by the flexible pressing portion 53 of the rotating tube 50 (as shown in FIG. 5) to release the connector 24, hence the returning spring 27 pushes the pushing member 26 of the connector 24, and then each extension 263 of the pushing member 26 contacts with the two second outer protrusions 64 of each stopping set of the driving sheath 60, thus starting to trigger the lancet. Because the two second outer protrusions 64 of each stopping set of the driving sheath 60 are stopped by each second inner protrusion 52 of the rotating tube 50, and each extension 263 of the pushing member 26 contacts with the two second outer protrusions 64 of each stopping set of the driving sheath 60, as shown in FIG. 4, even though the connector 24 is pressed, the triggering shaft 22 does not operate, thus avoiding retracting the lancet.

Figure 7:
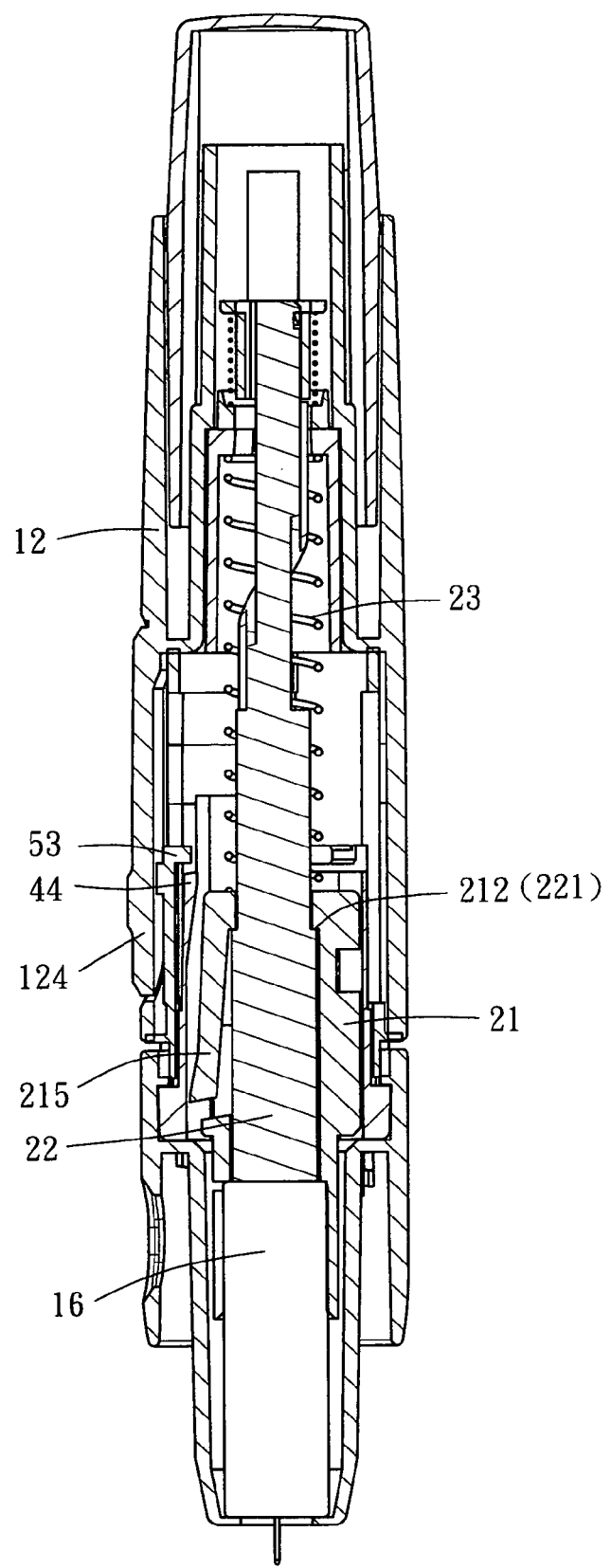
FIG. 7 is also another cross sectional view showing the operation of the blood sampling device according to the preferred embodiment of the present invention.

When starting trigger the lancet, a starting switch 124 of the body 12 is pressed by user's finger (as illustrated in FIGS. 2 to 7) so that the starting switch 124 presses the flexible pressing portion 53 of the rotating tube 50, and the flexible pressing portion 53 presses the abutting portion 44 of the lancet holder 21, hence the abutting portion 44 disengages from the launching portion 215 of the lancet holder 21, the resilient element 23 pushes the lancet holder 21 to drive the triggering shaft 22 by engaging the first inner shoulder 212 of the lancet holder 21 with the first outer shoulder 221 of the triggering shaft 22, as illustrated in FIG. 7, thus triggering the lancet 16.

Figure 8:
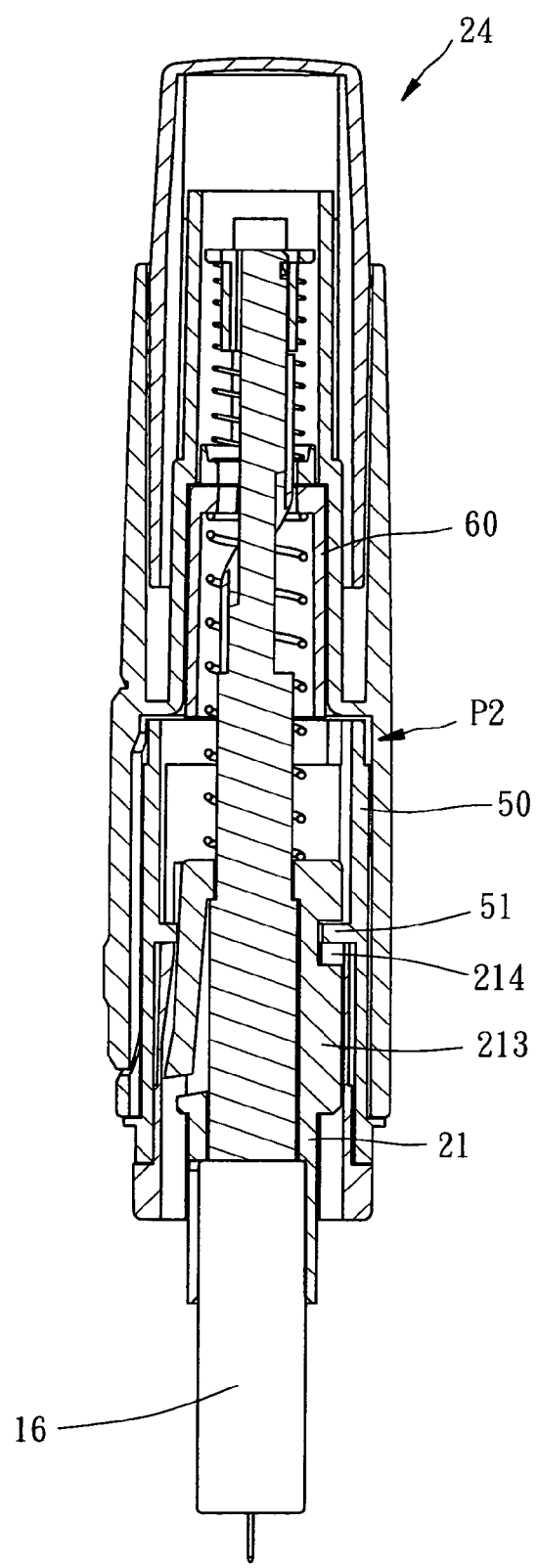
FIG. 8 is still another cross sectional view showing the operation of the blood sampling device according to the preferred embodiment of the present invention.
Figure 10:
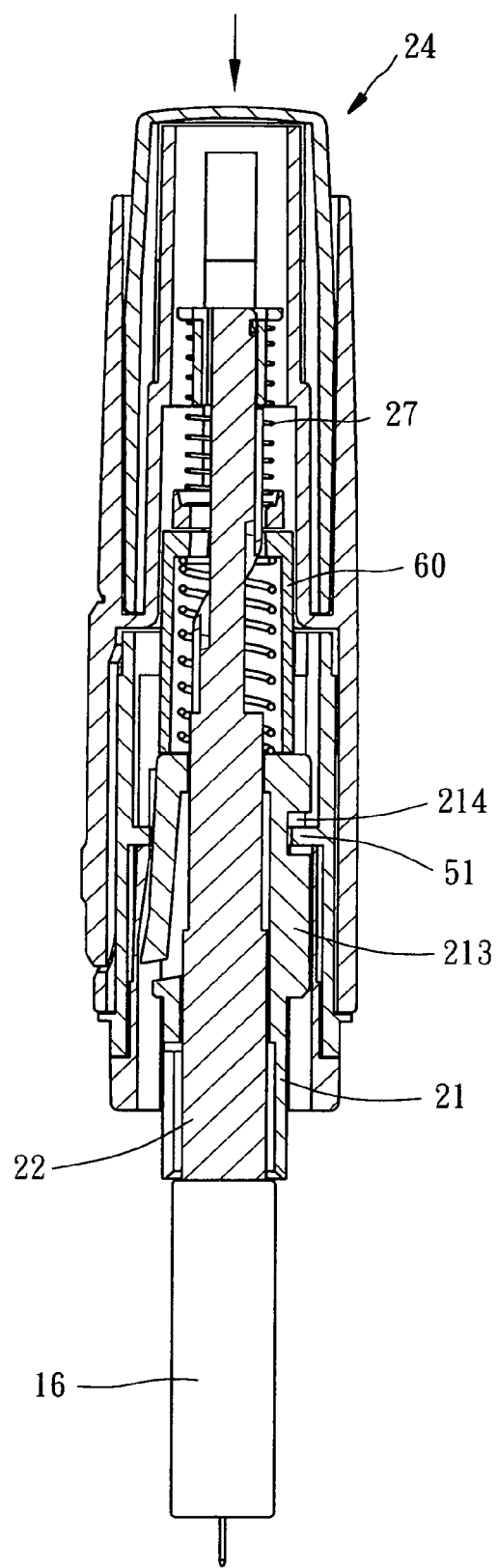
FIG. 10 is also another cross sectional view showing the operation of the blood sampling device according to the preferred embodiment of the present invention.

As desiring to retract the lancet, the fitting tube 14 is removed to expose the lancet 16, and the rotating tube 50 is rotated toward the retracting position P2, as shown in FIG. 8, then the lancet 16 is inserted into a storing sleeve (not shown). It is to be noted that the lancet holder 21 does not move, because it is limited by the rotating tube 50. In addition, the driving sheath 60 is not stopped by the rotating tube 50 (as shown in FIG. 9), so while pressing the connector 24, the pushing member 26 pushes the driving sheath 60 and the triggering shaft 22 downwardly, such that the triggering shaft 22 pushes the lancet 16 out of the through orifice 211 of the lancet holder 21. With reference to FIG. 10, after retracting the lancet, the connector 24 is released so that the returning spring 27 pushes the triggering shaft 22 back to the through hole 211 of the lancet holder 21. In the meantime, the lancet 16 is fixed in the storing sleeve so that it is discarded with the storing sleeve. Referring to FIG. 8, during retracting the lancet, since the lancet holder 21 engages with the rotating tube 50, even though the triggering shaft 22 is pulled by the connector 24, the lancet holder 21 cannot be pulled toward the starting position, thus avoiding triggering the lancet.

Thereby, the protecting mechanism 18 of the present invention prevents a removal of the lancet by using the switching assembly 30 while triggering the lancet and avoids triggering the lancet while retracting the lancet.

While the preferred embodiments of the invention have been set forth for the purpose of disclosure, modifications of the disclosed embodiments of the invention and other embodiments thereof may occur to those skilled in the art. Accordingly, the appended claims are intended to cover all embodiments which do not depart from the spirit and scope of the invention.

What is claimed is:

1. A protecting mechanism for a blood sampling device comprising:
    a trigger unit including a lancet holder, a triggering shaft, and a resilient element, the lancet holder having a launching portion and a first outer protrusion opposite the launching portion, the lancet holder also having a through orifice defined therein and a first inner shoulder defined on a top end of the through orifice, wherein a bottom end of the triggering shaft moves in the through orifice, and the triggering shaft has a first outer shoulder arranged on an outer wall thereof to engage with the first inner shoulder of the lancet holder, the resilient element fitted with the triggering shaft and abutting against the lancet holder by way of a bottom end of the resilient element; and
    a switching assembly including a fixing jacket, a rotating tube, and a driving sheath, the fixing jacket being fitted with the lancet holder and having an abutting portion, the rotating tube being rotatably fitted with the fixing jacket between a starting position and a retracting position, and the rotating tube having a first inner protrusion arranged on an inner wall thereof and having two opposite second inner protrusions formed on the inner wall thereof, the driving sheath being fitted on a top end of the triggering shaft and contacting with a top end of the resilient element, and the driving sheath having two stopping sets arranged on an outer wall thereof, wherein each stopping set has two second outer protrusions;
    wherein the lancet holder further includes a cutout defined on the first outer protrusion, such that when the rotating tube is located at the starting position, the first inner protrusion of the rotating tube moves away from the cutout of the lancet holder to remove from the first outer protrusion of the lancet holder, and when the rotating tube is located at the retracting position, the first inner protrusion of the rotating tube extends into the cutout of the lancet holder to engage with the first outer protrusion of the lancet holder.

2. The protecting mechanism for the blood sampling device as claimed in claim 1, wherein the rotating tube further has a flexible pressing portion formed on the outer wall thereof, such that when the rotating tube is located at the starting position, the flexible pressing portion presses the launching portion of the lancet holder.

3. The protecting mechanism for the blood sampling device as claimed in claim 1, wherein the trigger unit further includes a connector fitted with the top end of the triggering shaft and abuts against the driving sheath.

4. The protecting mechanism for the blood sampling device as claimed in claim 3, wherein the top end of the triggering shaft extends out of the through orifice of the lancet holder and has a second outer shoulder above the first outer shoulder, the connector has a pushing member, and the pushing member has two opposite second inner shoulders arranged on an inner wall thereof to engage with the second outer shoulder of the triggering shaft, and the pushing member also has two opposite extensions extending outwardly from an outer wall thereof, wherein each extension contacts with the two second outer protrusions of each stopping set of the driving sheath.

5. The protecting mechanism for the blood sampling device as claimed in claim 4, wherein the connector has a housing, and the housing has an aperture and two opposite retainers formed on a peripheral wall of the aperture, wherein each extension has a locking portion for engaging with each retainer of the housing.

6. The protecting mechanism for the blood sampling device as claimed in claim 4, wherein the trigger unit further includes a cap and a returning spring, and the cap is fitted with the top end of the triggering shaft, the returning spring is fitted on the triggering shaft and is biased against the pushing member and the cap.

7. A protecting mechanism for a blood sampling device comprising:
    a trigger unit including a lancet holder, a triggering shaft, and a resilient element, the lancet holder having a launching portion and a first outer protrusion opposite the launching portion, the lancet holder also having a through orifice defined therein and a first inner shoulder defined on a top end of the through orifice, wherein a bottom end of the triggering shaft moves in the through orifice, and the triggering shaft has a first outer shoulder arranged on an outer wall thereof to engage with the first inner shoulder of lancet holder, the resilient element fitted with the triggering shaft and abutting against the lancet holder by way of a bottom end of the resilient element; and
    a switching assembly including a fixing jacket, a rotating tube, and a driving sheath, the fixing jacket being fitted with the lancet holder and having an abutting portion, the rotating tube being rotatably fitted with the fixing jacket between a starting position and a retracting position, and the rotating tube having a first inner protrusion arranged on an inner wall thereof and having two opposite second inner protrusions formed on the inner wall thereof, the driving sheath being fitted on a top end of the triggering shaft and contacting with a top end of the resilient element, and the driving sheath having two stopping sets arranged on an outer wall thereof, wherein each stopping set has two second outer protrusions;

wherein the rotating tube further has a flexible pressing portion formed on the outer wall thereof, such that when the rotating tube is located at the starting position, the flexible pressing portion presses the launching portion of the lancet holder.

8. The protecting mechanism for the blood sampling device as claimed in claim 7, wherein the trigger unit further includes a connector fitted with the top end of the triggering shaft and abuts against the driving sheath.

9. The protecting mechanism for the blood sampling device as claimed in claim 8, wherein the top end of the triggering shaft extends out of the through orifice of the lancet holder and has a second outer shoulder above the first outer shoulder, the connector has a pushing member, and the pushing member has two opposite second inner shoulders arranged on an inner wall thereof to engage with the second outer shoulder of the triggering shaft, and the pushing member also has two opposite extensions extending outwardly from an outer wall thereof, wherein each extension contacts with the two second outer protrusions of each stopping set of the driving sheath.

10. The protecting mechanism for the blood sampling device as claimed in claim 9, wherein the connector has a housing, and the housing has an aperture and two opposite retainers formed on a peripheral wall of the aperture, wherein each extension has a locking portion for engaging with each retainer of the housing.

11. The protecting mechanism for the blood sampling device as claimed in claim 9, wherein the trigger unit further includes a cap and a returning spring, and the cap is fitted with the top end of the triggering shaft, the returning spring is fitted on the triggering shaft and is biased against the pushing member and the cap.

12. A protecting mechanism for a blood sampling device comprising:
a trigger unit including a lancet holder, a triggering shaft, and a resilient element, the lancet holder having a launching portion and a first outer protrusion opposite the launching portion, the lancet holder also having a through orifice defined therein and a first inner shoulder defined on a top end of the through orifice, wherein a bottom end of the triggering shaft moves in the through orifice, and the triggering shaft has a first outer shoulder arranged on an outer wall thereof to engage with the first inner shoulder of lancet holder, the resilient element fitted with the triggering shaft and abutting against the lancet holder by way of a bottom end of the resilient element; and a switching assembly including a fixing jacket, a rotating tube, and a driving sheath, the fixing jacket being fitted with the lancet holder and having an abutting portion, the rotating tube being rotatably fitted with the fixing jacket between a starting position and a retracting position, and the rotating tube having a first inner protrusion arranged on an inner wall thereof and having two opposite second inner protrusions formed on the inner wall thereof, the driving sheath being fitted on a top end of the triggering shaft and contacting with a top end of the resilient element, and the driving sheath having two stopping sets arranged on an outer wall thereof, wherein each stopping set has two second outer protrusions;

wherein the trigger unit further includes a connector fitted with the top end of the triggering shaft and abuts against the driving sheath.

13. The protecting mechanism for the blood sampling device as claimed in claim 12, wherein the top end of the triggering shaft extends out of the through orifice of the lancet holder and has a second outer shoulder above the first outer shoulder, the connector has a pushing member, and the pushing member has two opposite second inner shoulders arranged on an inner wall thereof to engage with the second outer shoulder of the triggering shaft, and the pushing member also has two opposite extensions extending outwardly from an outer wall thereof, wherein each extension contacts with the two second outer protrusions of each stopping set of the driving sheath.

14. The protecting mechanism for the blood sampling device as claimed in claim 13, wherein the connector has a housing, and the housing has an aperture and two opposite retainers formed on a peripheral wall of the aperture, wherein each extension has a locking portion for engaging with each retainer of the housing.

15. The protecting mechanism for the blood sampling device as claimed in claim 13, wherein the trigger unit further includes a cap and a returning spring, and the cap is fitted with the top end of the triggering shaft, the returning spring is fitted on the triggering shaft and is biased against the pushing member and the cap.

* * * * *